US010565745B2

(12) United States Patent
Wang

(10) Patent No.: US 10,565,745 B2
(45) Date of Patent: Feb. 18, 2020

(54) FAST PROJECTION MATCHING METHOD FOR COMPUTED TOMOGRAPHY IMAGES

(71) Applicant: National Synchrotron Radiation Research Center, Hsinchu (TW)

(72) Inventor: Chun-Chieh Wang, Hsinchu (TW)

(73) Assignee: NATIONAL SYNCHROTRON RADIATION RESEARCH CENTER, Hsinchu (TW)

(*) Notice: Subject to any disclaimer, the term of this patent is extended or adjusted under 35 U.S.C. 154(b) by 81 days.

(21) Appl. No.: 16/022,870

(22) Filed: Jun. 29, 2018

(65) Prior Publication Data

US 2019/0156523 A1    May 23, 2019

(30) Foreign Application Priority Data

Nov. 17, 2017  (TW) .............................. 106140007 A

(51) Int. Cl.
G06T 11/00  (2006.01)
G06T 7/00   (2017.01)
A61B 6/00   (2006.01)
G01N 23/046 (2018.01)
A61B 6/03   (2006.01)

(52) U.S. Cl.
CPC .......... G06T 11/003 (2013.01); G06T 7/0012 (2013.01); G06T 11/008 (2013.01); A61B 6/032 (2013.01); A61B 6/5235 (2013.01); G01N 23/046 (2013.01); G06T 2207/10081 (2013.01)

(58) Field of Classification Search
CPC ..................................................... G06T 11/006
See application file for complete search history.

(56) References Cited

U.S. PATENT DOCUMENTS

| | | | | | |
|---|---|---|---|---|---|
| 5,565,669 | A  * | 10/1996 | Liu ...................... | G06K 7/14 |
| | | | | 235/462.08 |
| 6,850,585 | B2 * | 2/2005 | Hsieh ................... | A61B 6/481 |
| | | | | 378/15 |
| 7,359,535 | B2 * | 4/2008 | Salla .................... | A61B 6/032 |
| | | | | 378/4 |
| 7,366,278 | B2 * | 4/2008 | Fu ....................... | G06T 11/008 |
| | | | | 345/419 |
| 7,885,371 | B2 * | 2/2011 | Thibault ............... | G06T 11/006 |
| | | | | 378/4 |
| 8,565,860 | B2 * | 10/2013 | Kimchy ................ | A61B 5/055 |
| | | | | 250/363.01 |
| 9,501,839 | B1 * | 11/2016 | Korchev ............... | G06T 5/002 |
| 9,763,640 | B2 * | 9/2017 | Li ........................ | A61B 6/022 |

(Continued)

Primary Examiner — Cindy Trandai
(74) Attorney, Agent, or Firm — Birch, Stewart, Kolasch & Birch, LLP

(57) ABSTRACT

A fast projection matching method for computed tomography (CT) images is provided. The method mainly bases on an iterative algorithm. The algorithm simplifies a traditional issue of three-dimensional projection matching into a two-dimensional projection-matching problem by pre-correcting the Y-axis offset and $\phi$ shift of each projection intensity image using common-line concept, thereby making the complex CT alignment processing faster and more reliable. This majorly reduces the hardware requirements for CT and data processing, which facilitates the applications in other three dimensional tomographic techniques, such as X-ray micro-CT or electron tomography.

7 Claims, 12 Drawing Sheets
(1 of 12 Drawing Sheet(s) Filed in Color)

(56) References Cited

U.S. PATENT DOCUMENTS

| | | | |
|---|---|---|---|
| 9,858,690 B2* | 1/2018 | Chen | G06T 11/006 |
| 10,373,349 B2* | 8/2019 | Koehler | G06T 11/006 |
| 2002/0085219 A1* | 7/2002 | Ramamoorthy | G06T 15/10 |
| | | | 358/1.9 |
| 2003/0099405 A1* | 5/2003 | Avinash | G06T 5/002 |
| | | | 382/260 |
| 2006/0002615 A1* | 1/2006 | Fu | A61B 6/5235 |
| | | | 382/254 |
| 2008/0075375 A1* | 3/2008 | Unal | G06K 9/621 |
| | | | 382/243 |
| 2010/0142795 A1* | 6/2010 | Crockett | G06K 9/186 |
| | | | 382/140 |
| 2012/0301004 A1* | 11/2012 | Kingston | A61B 6/032 |
| | | | 382/131 |
| 2012/0305780 A1* | 12/2012 | Thiruvenkadam | A61B 6/037 |
| | | | 250/363.03 |
| 2013/0343673 A1* | 12/2013 | Pal | G06T 11/003 |
| | | | 382/298 |
| 2017/0079608 A1* | 3/2017 | Hamill | A61B 6/5235 |
| 2018/0211416 A1* | 7/2018 | Chen | A61B 6/5211 |
| 2019/0005162 A1* | 1/2019 | Kwon | G06F 17/5009 |
| 2019/0137401 A1* | 5/2019 | Ozeki | G02B 21/06 |

* cited by examiner

FAST PROJECTION MATCHING METHOD FOR COMPUTED TOMOGRAPHY IMAGES

CROSS-REFERENCE TO RELATED APPLICATION

This non-provisional application claims priority under 35 U.S.C. § 119(a) to Patent Application No. 106140007 filed in Taiwan, R.O.C. on Nov. 17, 2017, the entire contents of which are hereby incorporated by reference.

BACKGROUND

Related Field

The instant disclosure relates to a fast projection matching method for computed tomography images.

Related Art

Three-dimensional (3D) computed tomography (CT) has broad applications in the fields of medical and material structural measurements. Currently, the way to reconstruct 3D images with CT technology is to obtain by capturing sample projection images in different directions and conducting a 3D image-reconstruction algorithm. However, the accuracy of 3D image-reconstruction significantly relates to the spatial positioning accuracy of these projection images. Along with the improvement of the spatial resolution in image technologies, the accuracy of the sample carrier cannot achieve the requirement of precise positioning when the resolution requires nano-level accuracy. Therefore, the support of image alignment algorithm becomes very important. Although the minor mechanical differences at each rotation angle of the sample carrier is correctable by sensitive and accurate sensing and feedback systems, conventional mechanical alignment procedures are still complex and time-consuming. Besides, unexpected image drifting could occur due to the heat effects on the sample or system generated by the illumination of detecting lights while capturing images. Such integrated image positioning difference is not resolvable by mechanical alignments.

In tradition, positional markers are applied as base points for image alignment by disposing such positional markers on or near the target object. Such method of adding additional positional markers on the target object may obtain images with accurate image alignments by hand alignments or by automatic particle tracking algorithm. However, hand alignments consume work force and time, and the additional positional markers do not always appear at the expected positions may cause troubles when selecting the observing area of the target object in interest.

Therefore, experts propose several non-marker automatic image alignment algorithms to resolve the issues above. Other algorithms are introduced as well. However, some algorithms do not consider and correct the mechanism for the actual movements of the object during rotations, and some of which do not apply accurate methods for correcting the rotation offsets of the object. Some other algorithms are too complex. These conventional algorithms have a major problem of massive statistics and computations, which greatly increase the hardware specification of computing requirements and limit the efficiency of processing CT data.

SUMMARY

Accordingly, the instant disclosure provides embodiments for a projection matching method for computed tomography images.

In an embodiment, a projection matching method for computed tomography images includes the following steps. Step (a) captures a first XY projection intensity image of an object on an XY plane with the object rotating at a first angle corresponding to a rotation axis. Step (b) captures a second XY projection intensity image of the object on the XY plane with the object rotating at a second angle corresponding to the rotation axis. Step (c) conducts an integral calculation, along an X-axis direction, on the first XY projection intensity image for calculating a first intensity distribution of the object at the first angle. Step (d) conducts the integral calculation, along the X-axis direction, on the second XY projection intensity image for calculating a second intensity distribution of the object at the second angle. Step (e) compares whether the first intensity distribution and the second intensity distribution are identical. Step (f), when the first intensity distribution and the second intensity distribution are not identical, rotates the first XY projection intensity image along a Z-axis direction and moving along a Y-axis direction to obtain a first XY projection intensity-modified image, and rotates the second XY projection intensity image along the Z-axis direction and moving along the Y-axis direction to obtain a second XY projection intensity-modified image. Step (g) conducts the integral calculation along the X-axis direction on the first XY projection intensity-modified image for calculating a first intensity-modified distribution of the object at the first angle, and also conducts the integral calculation along the X-axis direction on the second XY projection intensity-modified image for calculating a second intensity-modified distribution of the object at the second angle. Step (h) balances a difference value between the first intensity-modified distribution and the second intensity-modified distribution. In Step (i), when the difference value between the first intensity-modified distribution and the second intensity-modified distribution is greater than a first preset value, the Step (f) to the Step (h) repeat until the difference value between the first intensity-modified distribution and the second intensity-modified distribution is smaller than the first preset value; and when the difference value of the first intensity-modified distribution and the second intensity-modified distribution is smaller than the first preset value, defines the first intensity-modified distribution or the second intensity-modified distribution as an initial intensity base distribution. Step (j) captures a third XY projection intensity image of the object on the XY plane with the object rotating corresponding to the rotation axis at every angle from 0 degree to 180 degree by a preset angle interval. Step (k) conducts the integral calculation, along the X-axis direction, on the third XY projection intensity image of the object at each said angle for calculating a third intensity distribution of the object at each said angle. Step (l) rotates the third XY projection intensity image of the object along the Z-axis direction at each said angle, for producing a plurality of third XY projection intensity-modified images of the object at each said angle. Step (m) conducts the integral calculation, along the X-axis direction, on the third XY projection intensity-modified images of the object at each said angle, for calculating a plurality of third intensity-modified distributions of the object at each said angle. Step (n) calculates a first minimum difference intensity distribution with the minimum difference from the third intensity distributions and the third intensity-modified distributions to the initial intensity base distribution. Step (o) averages the first minimum difference intensity distribution of the object at each said angle for producing a first average intensity base distribution. Step (p) calculates a second minimum difference intensity distribution of the object at each said angle with the minimum difference from the third intensity distributions and the third intensity-modified distributions to the first average intensity base distribution. Step (q) averages the second minimum difference intensity distribution of the object at each said angle for producing a second average intensity base distribution. Step (r) determines whether the difference value between the first average intensity base distribution and the second average intensity base distribution is smaller than a second preset value. And in Step (s), when the difference value between the first average intensity base distribution and the second average intensity base distribution is smaller than the second preset value, rectifies an offset in the X-axis direction of the third XY projection intensity image or the third XY projection intensity-modified image in correspondence with the third minimum difference intensity distribution of the object at each said angle for producing the computed tomography images.

BRIEF DESCRIPTION OF THE DRAWINGS

The patent or application file contains at least one color drawing. Copies of this patent or patent application publication with color drawing will be provided by the USPTO upon request and payment of the necessary fee. The disclosure will become more fully understood from the detailed description given herein below for illustration only, and thus not limitative of the disclosure, wherein.

DETAILED DESCRIPTION

Figure 1:
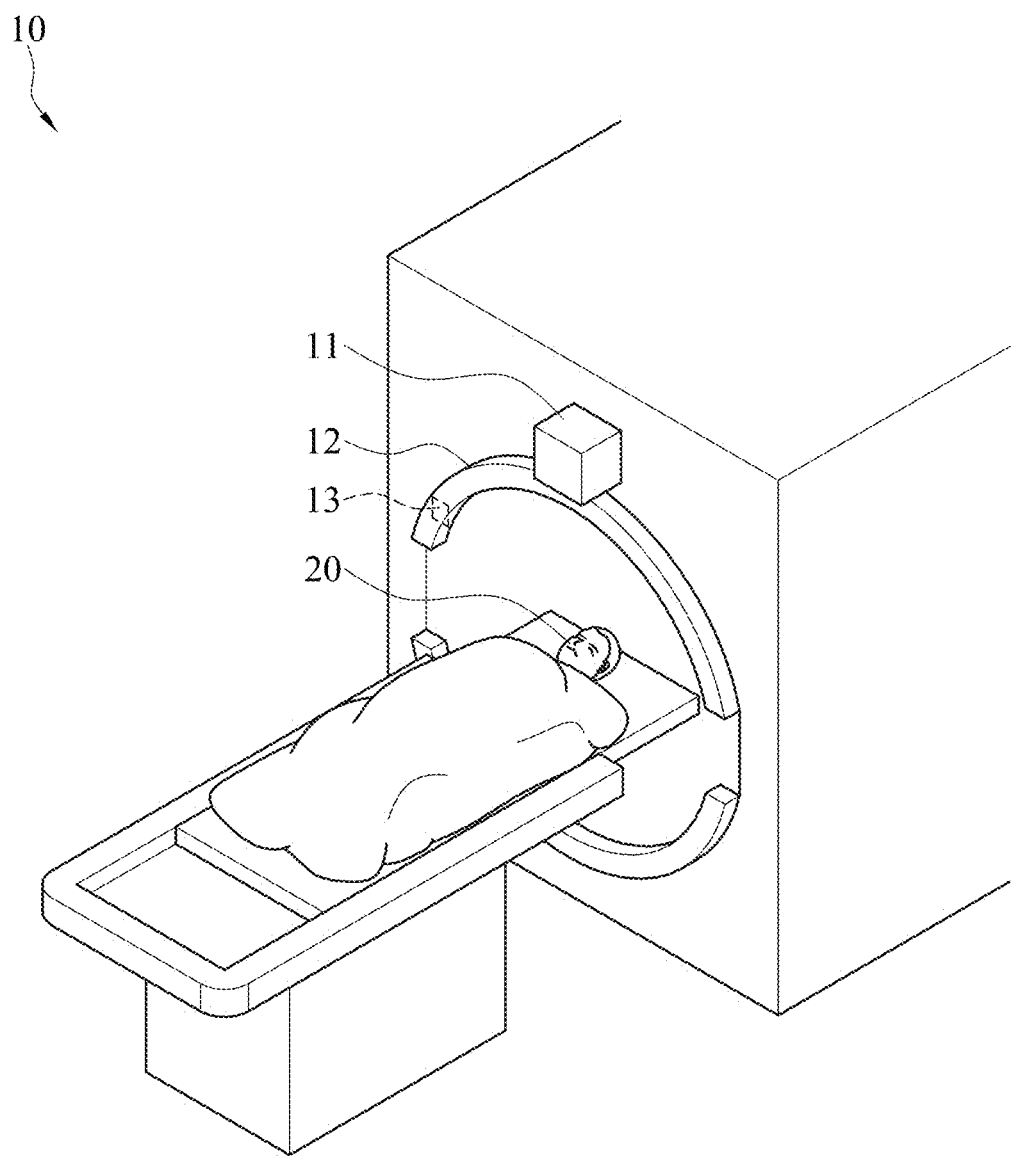
FIG. 1 illustrates an explanatory perspective view of a computed tomography apparatus 1 adapted for a fast projection matching method for computed tomography images according to an embodiment of the instant disclosure.
Figure 2:
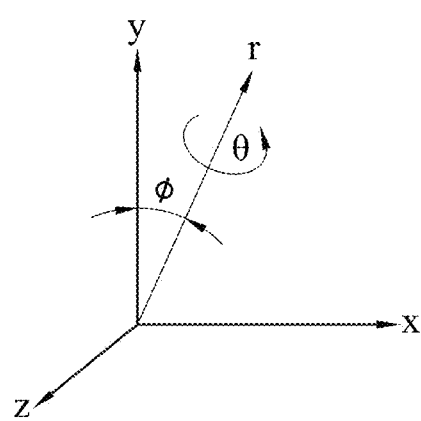
FIG. 2 illustrates an explanatory perspective view of a reference coordinate system.

FIG. 1 illustrates an explanatory perspective view of a computed tomography apparatus 1 adapted for a fast projection matching method for computed tomography images according to an embodiment of the instant disclosure. FIG. 2 illustrates an explanatory perspective view of a reference coordinate system. Referring to FIG. 1 and FIG. 2 jointly, the computed tomography apparatus 1 includes a light emitting unit 11, a data-receiving unit 12 and a processing unit 13. The processing unit 13 is coupled with the data-receiving unit 12. In an embodiment, the processing unit 13 may be installed in the data-receiving unit 12.

During the computed tomography process, the light emitting unit 11 and the data-receiving unit 12 and the object 20 may rotate corresponding to each other. For example, the object 20 is still, while the light emitting unit 11 and the data-receiving unit 12 rotate corresponding to the object 20; alternatively the light emitting unit 11 and the data-receiving unit 12 is still, while the object 20 rotates corresponding to the light emitting unit 11 and the data-receiving unit 12. The following examples based on that the light emitting unit 11 and the data-receiving unit 12 are still while the object 20 rotates corresponding to the light emitting unit 11 and the data-receiving unit 12. The object 20 in FIG. 1 takes a human body as an example, which is not meant to be a limitation to the instant disclosure; alternatively, the object 20 may be any articles or animals.

The light emitting unit 11 illuminates X-ray along a Z-axis direction towards the object 20, and the object 20 rotates corresponding to a rotation axis. The data-receiving unit 12 receives the X-ray passing through the object 20 to obtain a projection intensity image of the object 20 on a XY plane. The processing unit 13 computes with preset program codes according to the projection intensity image of the object 20 to produce a computed tomography image. Accordingly, the computed tomography apparatus 10 conducts a first correction procedure and a second correction procedure. In the first correction procedure, the computed tomography apparatus 10 conducts an iterative algorithm procedure based on a common-line algorithm concept, in which the first correction procedure rectifies the offset(s) of the projection intensity image of the object 20 due to the relative rotations between the object 20, the light emitting unit 11 and the data-receiving unit 12. The offsets include the offset in the vertical direction (Y-axis direction) and an offset angle φ on the XY plane in correspondence with the Y-axis direction. In addition, in the second correction procedure, the computed tomography apparatus 10 utilizes the concept of projection matching to conduct another iterative algorithm procedure. The second correction procedure rectifies the offset in the horizontal direction (X-axis direction) due to the relative rotations between the object 20, the light emitting unit 11 and the data-receiving unit 12. The following steps introduce the operation of the computed tomography apparatus 10.

Figure 3A:
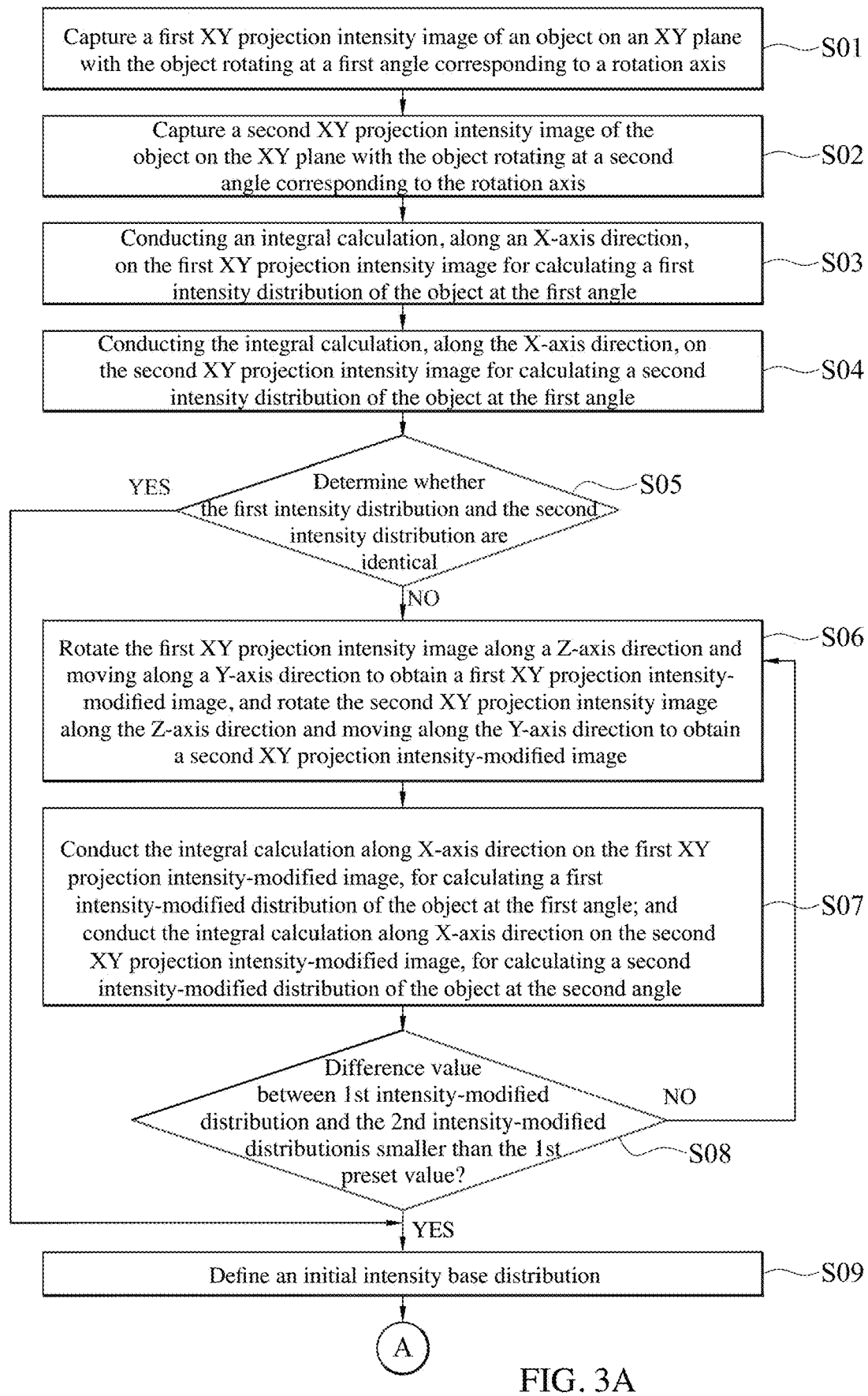
FIG. 3A illustrates an explanatory flowchart of a fast projection matching method for computed tomography images according to an embodiment of the instant disclosure.
Figure 3B:
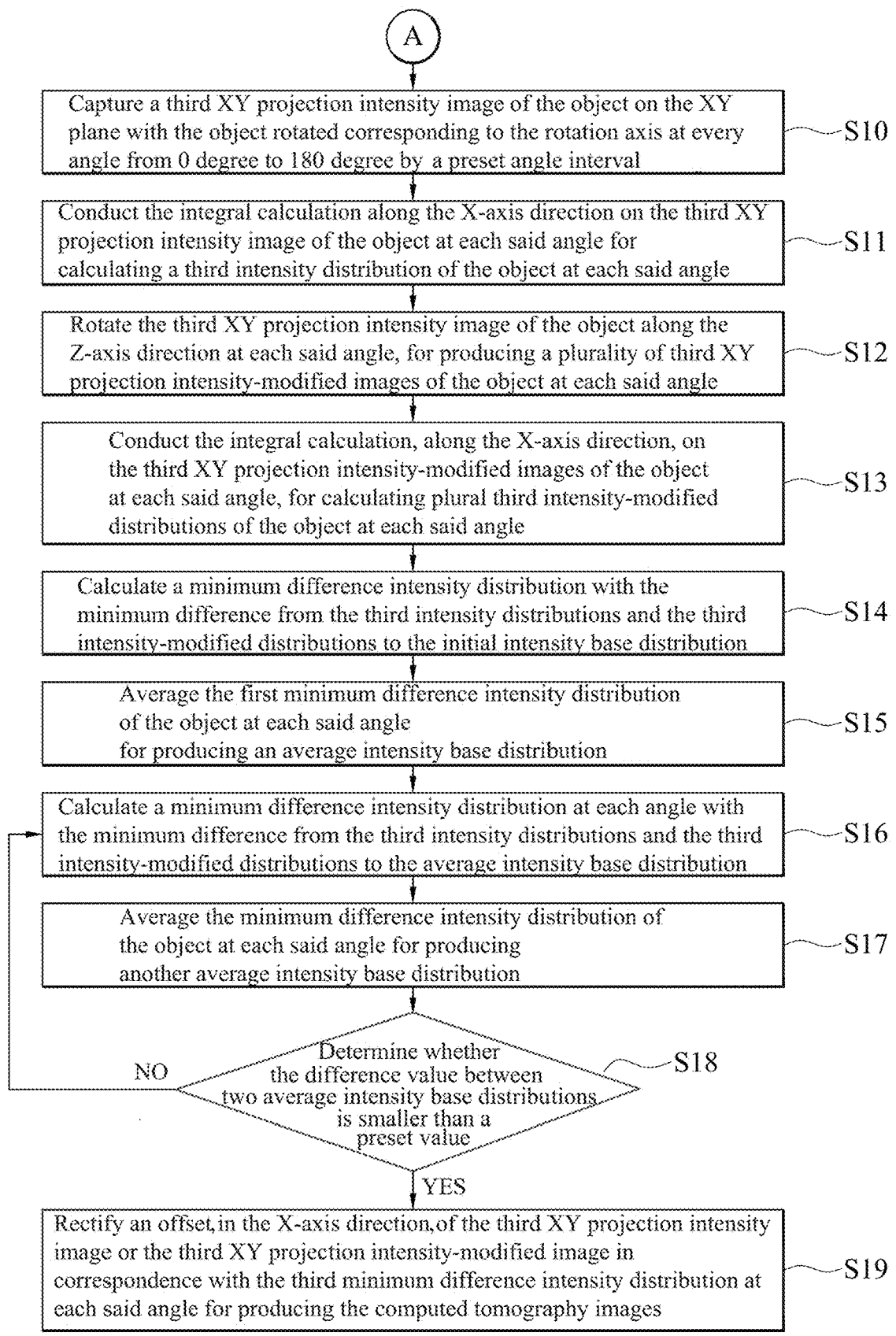
FIG. 3B illustrates an explanatory flowchart of a fast projection matching method for computed tomography images according to an embodiment of the instant disclosure.
Figure 4A:
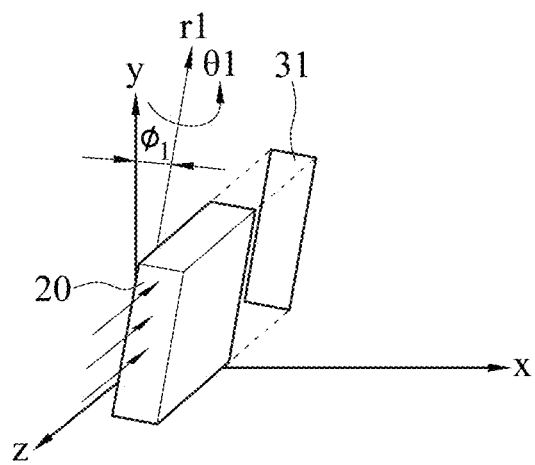
FIG. 4A illustrates an explanatory perspective view of a first XY projection intensity image according to an embodiment of the instant disclosure.
Figure 4B:
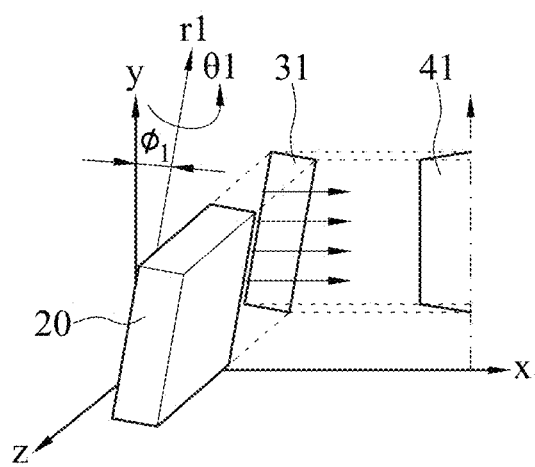
FIG. 4B illustrates an explanatory perspective view of a first XY projection intensity image conducted with an integral calculation by a processing unit based on Radon Transform.
Figure 4C:
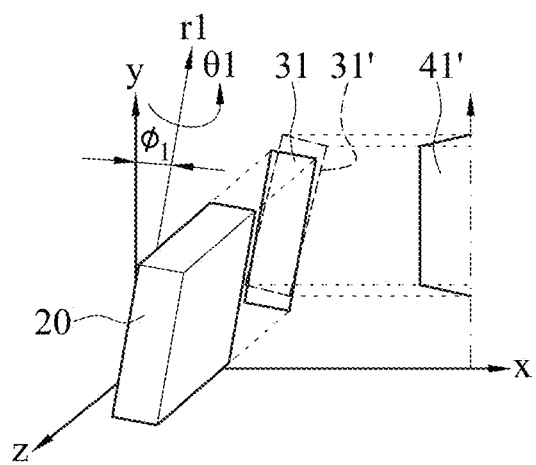
FIG. 4C illustrates an explanatory perspective view of a first XY projection intensity-modified image and a first intensity-modified distribution according to an embodiment of the instant disclosure.
Figure 5A:
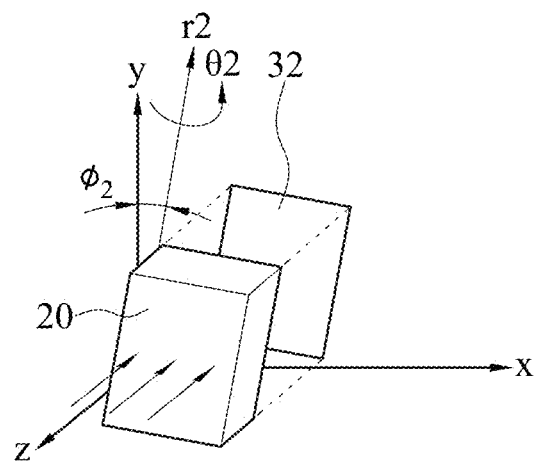
FIG. 5A illustrates an explanatory perspective view of a second XY projection intensity image according to an embodiment of the instant disclosure.

FIG. 3A and FIG. 3B illustrate explanatory flowcharts of projection matching methods for computed tomography images according to embodiments of the instant disclosure. FIG. 4A to FIG. 4C and FIG. 5A to FIG. 5C are explanatory views of a portion of the first correction procedure. Please refer to FIG. 1 to FIG. 3A-3B, FIG. 4A to FIG. 4C and FIG. 5A to FIG. 5C jointly. First of all, rotate the object 20 at a first angle corresponding to an rotation axis, and captures a XY projection intensity image (hereinafter "first XY projection intensity image") of the object 20 on the XY plane with the object 20 rotating at the first angle corresponding to the rotation axis (Step S01). Next, rotate the object 20 at a second angle corresponding to the rotation axis, and captures a XY projection intensity image (hereinafter "second XY projection intensity image") of the object 20 on the XY plane with the object 20 rotating at the second angle corresponding to the rotation axis (Step S02). Said first angle and second angle may be any angle from 0 degree to 180 degree, and the first angle and the second angle are not identical. For example, the first angle and the second angle may be 19 degree and 87 degree respectively, or the first angle and the second angle may be 0 degree and 90 degree respectively. As shown in FIG. 4A, which illustrates that the first XY projection intensity image 31 of the object 20 is formed on the XY plane with the object 20 rotating 0 degree to a first angle θ1 corresponding to the rotation axis r1. Besides, as shown in FIG. 5A, which illustrates that a second XY projection intensity image 32 of the object 20 is formed on the XY plane with the object 20 rotating 90 degree to a second angle θ2 corresponding to the rotation axis r2.

Figure 5B:
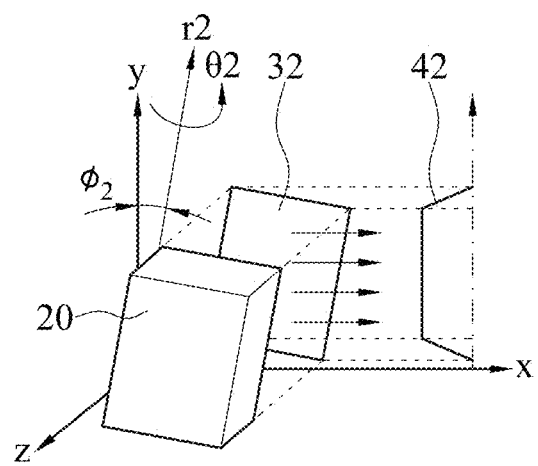
FIG. 5B illustrates an explanatory perspective view of a second XY projection intensity image conducted with an integral calculation by a processing unit based on Radon Transform.
Figure 5C:
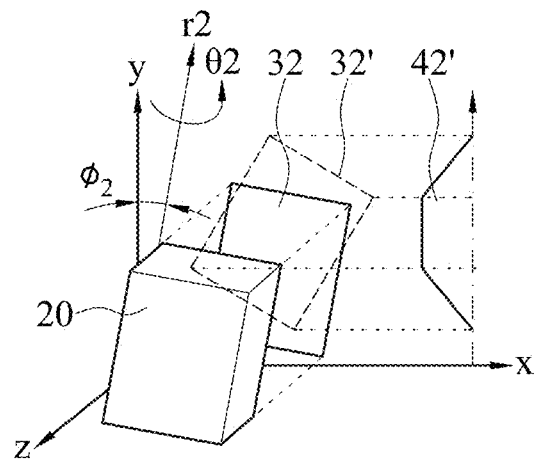
FIG. 5C illustrates an explanatory perspective view of a second XY projection intensity-modified image and a second intensity-modified distribution according to an embodiment of the instant disclosure.

Afterwards, the processing unit 13 conducts an integral calculation on the first XY projection intensity image 31 and the second XY projection intensity image 32. As shown in FIG. 4B, the processing unit 13 conducts the integral calculation along the X-axis direction on the first XY projection intensity image 31. The processing unit 13 then calculates a first intensity distribution 41 of the object 20 at the first angle θ1 (Step S03), and conducts the same integral calculation along X-axis direction on the second XY projection intensity image 32. As shown in FIG. 5B, the processing unit 13 calculates a second intensity distribution 42 of the object 20 at a second angle θ2 (Step S04). The processing unit 13 compares the first intensity distribution 41 and the second intensity distribution 42, to determine whether the first intensity distribution 41 and the second intensity distribution are identical (Step S05). When the first intensity distribution 41 and the second intensity distribution 42 are not identical (determined "NO"), as shown in FIG. 4C, rotate the first XY projection intensity image 31 within a preset angle along Z-axis direction and move the first XY projection intensity image 31 within a preset shift distance along Y-axis direction to obtain a rotated and/or shifted first XY projection intensity-modified image 31' (Step S06). In addition, as shown in FIG. 5C, rotate the second XY projection intensity image 32 within the preset angle along Z-axis direction, and move the second XY projection intensity image 32 within the preset shift distance along the Y-axis direction to obtain a rotated and/or shifted second XY projection intensity-modified image 32'(Step S07).

Figure 6A:
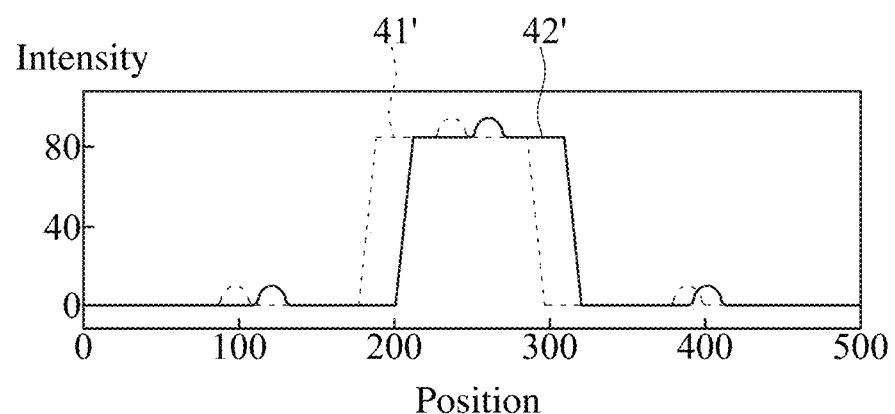
FIG. 6A illustrates an explanatory diagram of a first intensity-modified distribution and a second intensity-modified distribution according to an embodiment of the instant disclosure.
Figure 6B:
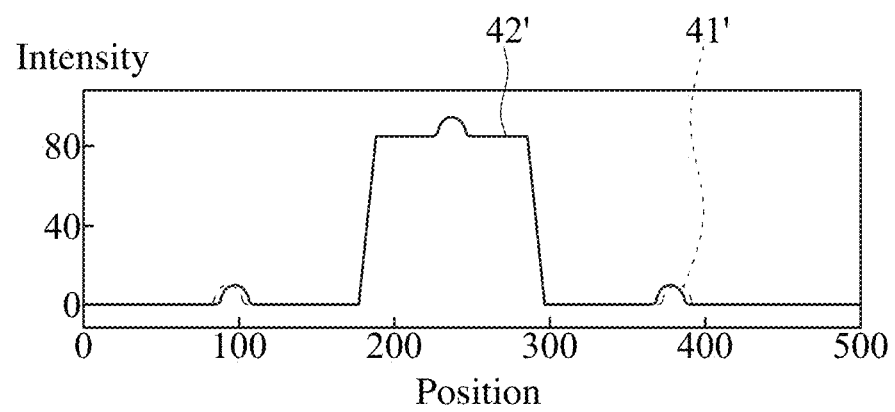
FIG. 6B illustrates an explanatory diagram of a first intensity-modified distribution and a second intensity-modified distribution according to another embodiment of the instant disclosure.

The processing unit 13 then conducts the integral calculation along X-axis direction on the first XY projection intensity-modified image 31', and conducts the integral calculation along X-axis direction on the second XY projection intensity-modified image 32', for calculating a first intensity-modified distribution 41' in correspondence with the first XY projection intensity-modified image 31' of the object 20 at the first angle θ1, and a second intensity-modified distribution 42' in correspondence with the second XY projection intensity-modified image 32' of the object 20 at the second angle θ2. The processing unit 13 balances the difference value between the first intensity-modified distribution 41' and the second intensity-modified distribution 42', to determine whether the difference value between the first intensity-modified distribution 41' and the second intensity-modified distribution 42' is smaller than a preset value (hereinafter "first preset value")(Step S08). When the difference value of the first intensity-modified distribution 41' and the second intensity-modified distribution 42' is greater than the first preset value, as the first intensity-modified distribution 41' and the second intensity-modified distribution 42' shown in FIG. 6A, the processing unit 13 repeatedly performs Step S06 to Step S08. Namely, the processing unit 13 moves the first XY projection intensity image 31 and the second XY projection intensity image 32 back and forth within the preset shift distance along Y-axis direction, as well as rotates the first XY projection intensity image 31 and the second XY projection intensity image 32 back and forth within the preset angle along Z-axis direction, until the processing unit 13 obtains the recalculated difference between the first intensity-modified distribution 41' and second intensity-modified distribution 42' respectively in correspondence with the first XY projection intensity-modified image 31' and second XY projection intensity-modified image 32' is smaller than the first preset value, as the explanatory first intensity-modified distribution 41' and second intensity-modified distribution 42' shown in FIG. 6B. When the difference between the first intensity-modified distribution 41' and the second intensity-modified distribution 42' is smaller than the first preset value, define the first intensity-modified distribution 41' or the second intensity-modified distribution 42' as an initial intensity base distribution (Step S09).

Subsequently, capture a XY projection intensity image (hereinafter "third XY projection intensity image") of the object 20 on the XY plane with the object 20 rotated corresponding to the rotation axis at every angle from 0 degree to 180 degree by a preset angle interval (Step S10). For instance, the above-mentioned preset angle interval may be a 1 degree. Then 181 sets of the third XY projection intensity image may generate from projecting the object 20 with the object 20 rotating by the preset angle interval of 1 degree. That is, to rotate the object 20 corresponding to the rotation axis by 0 degree, 1 degree, 2 degree . . . until 180 degree for each third XY projection intensity image at each said angle. Afterwards, conduct the integral calculation, along X-axis direction, on the third XY projection intensity image of the object 20 at each said angle for calculating a third intensity distribution (hereinafter "third intensity distribution") of the object at each said angle (Step S11). Taking the example with 181 sets of the third XY projection intensity images, after performing Step S11, the processing unit 13 calculates a third intensity distribution in one-by-one correspondence with each third XY projection intensity image of the 181 sets of the third XY projection intensity images.

Afterwards, rotate the third XY projection intensity image of the object 20 along the Z-axis direction at each angle from 0 degree to 180 degree, for producing multiple third XY projection intensity-modified images of the object 20 at each said angle (Step S12). Taking an example with 181 sets of the third XY projection intensity images, if the preset angle interval is set as 1 degree to produce 1 set of third XY projection intensity-modified images at each degree from 0 degree to 180 degree, after Step S12 is completely performed, we will obtain 181 sets of third XY projection intensity-modified images by rotating 181 sets of third XY projection intensity images. Similarly, conduct the integral calculation, along X-axis direction, on the third XY projection intensity-modified images of the object 20 at each said angle, and the processing unit 13 then calculates object 20 plural third intensity-modified distributions at each said angle (Step S13), with each of the intensity-modified distributions in one-by-one correspondence with each of the third XY projection intensity-modified images.

The processing unit 13 then calculates a first minimum difference intensity distribution with the minimum difference from the third intensity distributions and the third intensity-modified distributions to the initial intensity base distribution (Step S14). In other words, the first minimum difference intensity distribution is selected from one of the third intensity distributions and the third intensity-modified distributions, and the minimum difference intensity distribution is the one, among the third intensity distributions and the third intensity-modified distributions, closest to the initial intensity base distribution. Accordingly, within 0 degree to 180 degree, the processing unit 13 calculates 181 sets of the first minimum difference intensity distributions. The processing unit 13 next averages the 181 sets of the first minimum difference intensity distributions, for producing a first average intensity base distribution (Step S15). After the first average intensity base distribution is calculated, the processing unit 13 calculates a second minimum difference intensity distribution of the object 20 at each said angle with the minimum difference from the third intensity distributions and the third intensity-modified distributions to the first average intensity base distribution (Step S16), so as to perform a following iterative algorithm procedure. Similarly, the second minimum difference intensity distribution is selected from one of the third intensity distributions and the third intensity-modified distributions, and the second minimum difference intensity distribution is the one, among all the third intensity distributions and the third intensity-modified distributions, closest to the first average intensity base distribution. Accordingly, within 0 degree to 180 degree, the processing unit 13 calculates 181 sets of the second minimum difference intensity distributions. The processing unit 13 then averages the 181 sets of the second minimum difference intensity distributions, for producing a second average intensity base distribution (Step S17).

The processing unit 13 determines whether the difference value between the first average intensity base distribution and the second average intensity base distribution is smaller than a preset value (hereinafter "second preset value")(Step S18). When the difference value between the first average intensity base distribution and the second average intensity base distribution is smaller than the second preset value (determined "YES"), it means the average intensity base distribution is converged. Now the first correction procedure is complete, namely the shift offsets and offset angle φ of the projection intensity images of the object 20 on Y-axis direction have been rectified. The computed tomography apparatus 10 next performs the second correction procedure, in which the processing unit 13 rectifies an offset, in the X-axis direction, of the third XY projection intensity image or the third XY projection intensity-modified image in correspondence with the second minimum difference intensity distribution of the object at each angle from 0 to 180 degree (Step S19), for producing the computed tomography images.

In an embodiment, in Step S14, the processing unit 13 may apply a cross-correlation algorithm along Y-axis direction within a preset vertical distance range to align the third intensity distribution to the initial intensity base distribution, and align the third intensity-modified distribution to the initial intensity base distribution, for calculating the first minimum difference intensity distribution at each said angle. The preset vertical distance range may be the systematic maximum possible error value of the computed tomography apparatus 10.

In an embodiment, when the difference value between the first average intensity base distribution and the second average intensity base distribution is greater than the second preset value (determined [NO]), it means the average intensity base distribution is not converged yet. No the processing unit 13 calculates a minimum difference intensity distribution (hereinafter "third minimum difference intensity distribution") with the minimum difference from the third intensity distributions and the third intensity-modified distributions to the second average intensity base distribution of the object 20 at each said angle (Step S16). Namely, return to Step S16 to perform the iterative algorithm procedure of the first correction procedure. Similarly, the processing unit 13 generates 181 sets of the third minimum difference intensity distribution within 0 degree to 180 degree. The processing unit 13 averages the third minimum difference intensity distributions of the object 20 at each said angle for producing third average intensity base distribution (Step S17). The processing unit 13 then determines whether the difference value between the second average intensity base distribution and the third average intensity base distribution is smaller than the second preset value (Step S18). If the determination results in "YES", then terminate the iterative algorithm procedure; and the processing unit 13 will then perform Step S19 to rectify the shift offset, in X-axis direction, of the third XY projection intensity image or the third XY projection intensity-modified image in correspondence with the third minimum difference intensity distribution of the object 20 at each angle from 0 degree to 180 degree. If the determination results in "NO", then repeatedly perform Step S16 to Step S18, until the processing unit 13 determines in Step S18 that in Step S17 the difference between the two consecutive average intensity base distributions is smaller than the second preset value. Then the iterative algorithm procedure of the first correction procedure is ended.

Figure 7:
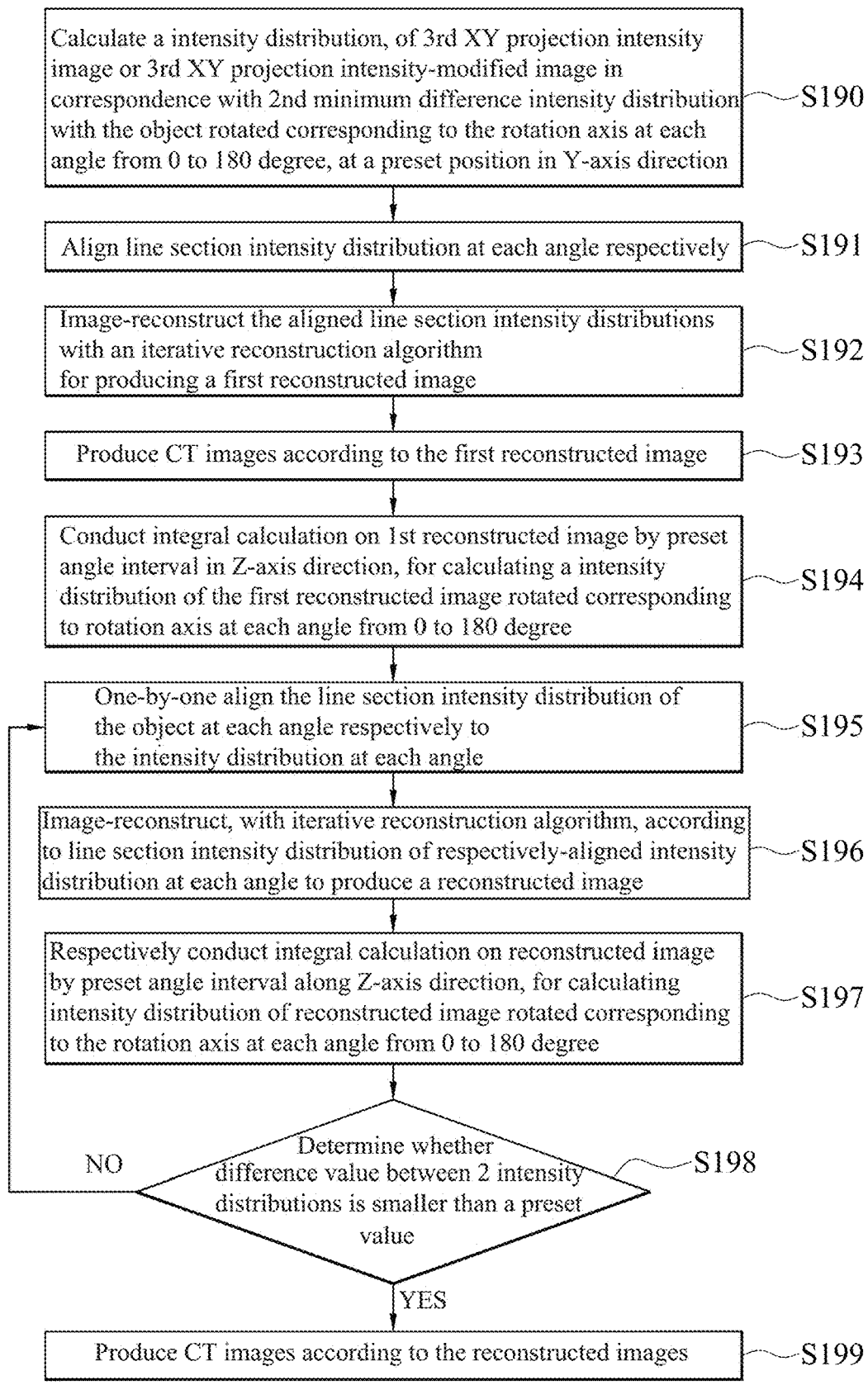
FIG. 7 illustrates an explanatory flowchart of the projection matching methods for computed tomography images in FIG. 3A and FIG. 3B according to an embodiment of the instant disclosure.
Figure 8:
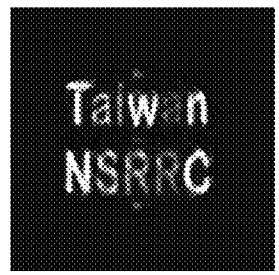
FIG. 8 illustrates an explanatory view of a computed tomography image produced by a processing unit according to a first reconstructed image of a text model object.

In the second correction procedure (namely Step S19), the processing unit 13 applies a cross-correlation algorithm to rectify the shift offset of the object 20 in X-axis direction. In detail, take the example that the processing unit 13, in Step S18, determines the difference value between the first average intensity base distribution and the second average intensity base distribution is smaller than the second preset value. Referring to FIG. 7, the processing unit 13 then, in Step S19, calculates an intensity distribution (hereinafter "line section intensity distribution"), of the third XY projection intensity image or the third XY projection intensity-modified image in correspondence with the second minimum difference intensity distribution with the object 20 rotated corresponding to the rotation axis at each said angle from 0 degree to 180 degree, at a preset position in the Y-axis direction (Step S190). For example, the preset position may be the Y-coordinate 30, and then the processing unit 13 calculates 181 sets of the line section intensity distributions at each said angle. Next, the processing unit 13 aligns the line section intensity distribution at each said angle respectively along X-axis direction with the cross-correlation algorithm (Step S191). While aligning, the processing unit 13 may utilize the line section intensity distribution of the object 20 rotated at 0 degree as an alignment base. And then, with the cross-correlation algorithm, align the line section intensity distribution at 1 degree to the line section intensity distribution at 0 degree. And then, with the cross-correlation algorithm, align the line section intensity distribution at 2 degree to the line section intensity distribution at 1 degree and so forth, until the processing unit 13 aligns the line section intensity distribution at 180 degree to the line section intensity distribution at 179 degree. After align the line section intensity distributions respectively, the processing unit 13 image-reconstructs, according to the 181 sets of line section intensity distributions with the line section intensity distribution at 0 degree followed by the consecutively aligned 180 sets of line section intensity distributions thereto, for producing a reconstructed image (hereinafter "first reconstructed image") (Step S192). Accordingly, the processing unit 13 may produce the computed tomography image according to the first reconstructed image (Step S193). As shown in FIG. 8, FIG. 8 is a computed tomography image of the text model object 20 produced from the first reconstructed image by the processing unit 13.

Figure 9:
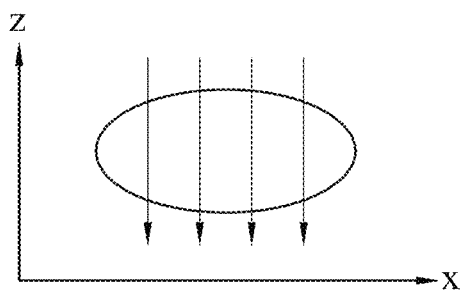
FIG. 9 illustrates an explanatory diagram of a first reconstructed image conducted with an integral calculation along a Z-axis direction by a processing unit based on Radon Transform.

Furthermore, in Step S19, the computed tomography apparatus 10 may, after reconstructing the first reconstructed image and according to the first reconstructed image, further rectifies the shift offset in the horizontal direction, of the third XY projection intensity image or the third XY projection intensity-modified image in correspondence with the second minimum difference intensity distribution, thereby further rectifying the offset of the object 20 in X-axis direction. More specifically, after reconstructing the first reconstructed image, as shown in FIG. 9, FIG. 9 introduces an example of a first reconstructed image, the processing unit 13 conducts an integral calculation on first reconstructed image based on radon transform along Z-axis direction and, the processing unit 13 calculates an intensity distribution (hereinafter "fourth intensity distribution") of the first reconstructed image that rotates corresponding to the rotation axis by the preset angle interval from 0 degree to 180 degree and each projects to X-axis direction (Step S194), thereby calculating 181 sets of the fourth intensity distributions of the first reconstructed image that rotates corresponding to the rotation axis at 0 degree, 1 degree, . . . till 180 degree and each projects to X-axis direction. Subsequently, the processing unit 13 aligns one-by-one the line section intensity distribution of the object at each said angle respectively along the X-axis direction, to the fourth intensity distribution at each said same angle (Step S195). The processing unit 13 aligns, the line section intensity distribution of the object 20 rotating at 0 degree, along X-axis direction, to the fourth intensity distribution of the first reconstructed image rotating at 0 degree; and then align the line section intensity distribution of the object 20 rotating at 1 degree, along X-axis direction, to the fourth intensity distribution of the first reconstructed image rotating at 1 degree, and so forth, until that the processing unit 13 aligns the line section intensity distribution of the object 20 rotating at 180 degree, along X-axis direction, to the fourth intensity distribution of the first reconstructed image rotating at 180 degree. The processing unit 13 image-reconstructs according to the 181 sets of the line section intensity distributions aligned to the 181 sets of the fourth intensity distributions by the iterative reconstruction algorithm, for producing a reconstructed image (hereinafter "second reconstructed image")(Step S196). The processing unit 13 further calculates, by the preset angle interval respectively, an intensity distribution (hereinafter "fifth intensity distribution") of the second reconstructed image that rotates corresponding to the rotation axis at each angle from 0 degree to 180 degree and each projects on X-axis direction (Step S197), for calculating 181 sets of the fifth intensity distributions corresponding to the range within 0 degree to 180 degree. The processing unit 13 determines the difference value between the fifth intensity distribution and the fourth intensity distribution is smaller than a third preset value (Step S198). When the differences between the 181 sets of the fifth intensity distributions and the 181 sets of the fourth intensity distributions are smaller than the third preset value respectively, it means the intensity distributions produced in the second procedure are converged, namely the shift offset in the X-axis direction have been rectified. Accordingly, the processing unit 13 produces the computed tomography image according to the second reconstructed image (Step S199).

In an embodiment, when the processing unit 13 in Step S198 determines the difference value between the fifth intensity distribution and the fourth intensity distribution is greater than the third preset value (determined "NO"), the processing unit 13 aligns one-by-one the line section intensity distribution at each said angle to the fifth intensity distribution at each said angle (Step S195), namely return to Step S195 and perform the iterative algorithm procedure of the second correction procedure. Afterwards, the processing unit 13 image-reconstructs according to the line section intensity distribution aligned to the fifth intensity distribution by the iterative reconstruction algorithm (Step S196), for producing a reconstructed image (hereinafter "third reconstructed image"). The processing unit 13 further calculates, by the preset angle interval, an intensity distribution (hereinafter "sixth intensity distribution") of the third reconstructed image that rotates corresponding to the rotation axis at each angle from 0 degree to 180 degree and projects on X-axis direction, for calculating 181 sets of the sixth intensity distribution. The processing unit 13 then determines whether the difference values respectively between the 181 sets of the sixth intensity distributions and the 181 sets of the fifth intensity distributions are smaller than the third preset value (Step S198). If the determination results in "YES", the processing unit 13 produces the computed tomography images according to the third reconstructed image (Step S199). If the determination results in "NO", then repeatedly perform Step S195 to Step S198, and the iterative algorithm procedure of the second correction procedure ends only until the processing unit 13 in Step S198 determines the difference between the two consecutively-calculated intensity distributions is smaller than the third preset value.

Figure 10:
FIG. 10 illustrates an explanatory diagram of a computed tomography image produced by conducting an iterative algorithm procedure according to a second correction procedure.

Referring to FIG. 10, FIG. 10 illustrates an explanatory diagram of a computed tomography image produced by conducting said iterative algorithm procedure according to a second correction procedure by the processing unit 13. Comparing FIG. 8 and FIG. 10, the computed tomography image produced by the iterative algorithm procedure has a higher clearness level than the computed tomography image produced in Step S193.

Figure 11A:
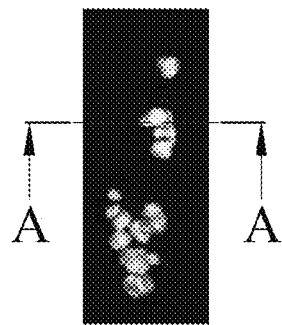
FIG. 11A illustrates an explanatory view of a 3D CT reconstructed image of a pyrite particle observed at an azimuth angle by applying the method according to an embodiment of the instance disclosure.
Figure 11B:
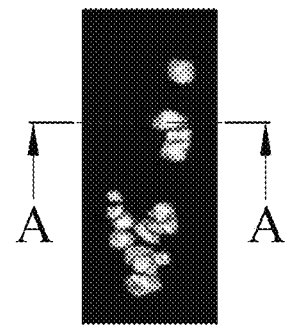
FIG. 11B illustrates an explanatory view of a 3D CT reconstructed image of a pyrite particle observed at an azimuth angle by applying a conventional alignment method.
Figure 11C:
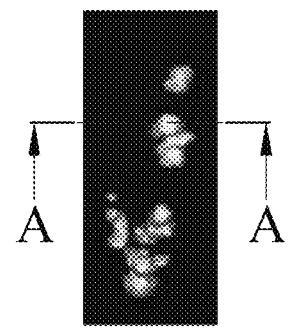
FIG. 11C illustrates an explanatory view of a 3D CT reconstructed image of a pyrite particle observed at an azimuth angle by applying a conventional alignment method.
Figure 11D:
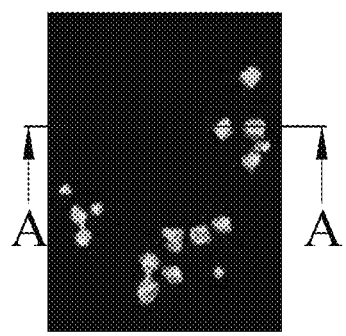
FIG. 11D illustrates an explanatory view of a 3D CT reconstructed image of a different pyrite particle observed at an azimuth angle by applying the method according to an embodiment of the instance disclosure.
Figure 11E:
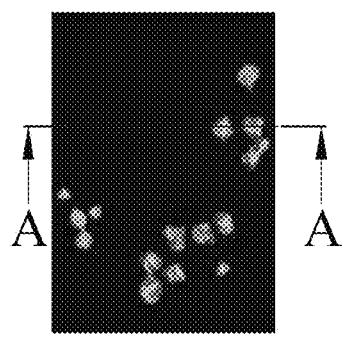
FIG. 11E illustrates an explanatory view of a 3D CT reconstructed image of a different pyrite particle observed at an azimuth angle by applying a conventional alignment method.
Figure 11F:
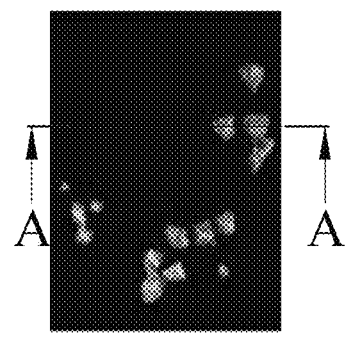
FIG. 11F illustrates an explanatory view of a 3D CT reconstructed image of a different pyrite particle observed at an azimuth angle by applying another conventional alignment method.
Figure 12A:
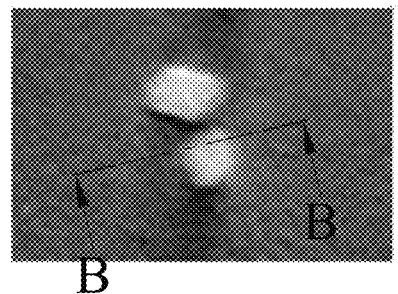
FIG. 12A illustrates an explanatory view of a sectional image along a sectional line A-A in FIGS. 11A and 11D.
Figure 12B:
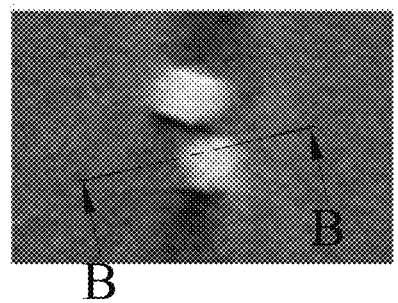
FIG. 12B illustrates an explanatory view of a sectional image along a sectional line A-A in FIGS. 11B and 11E.
Figure 12C:
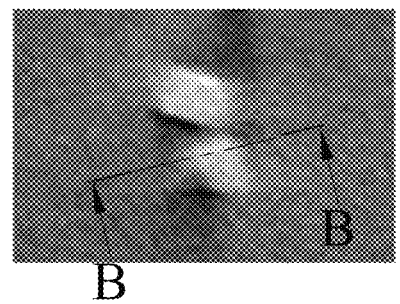
FIG. 12C illustrates an explanatory view of a sectional image along a sectional line A-A in FIGS. 11C and 11F.

Please jointly refer to FIG. 11A to FIG. 11F and FIG. 12A to FIG. 12C. FIG. 11A and FIG. 11D are respectively an explanatory view of a 3D CT reconstructed image of a pyrite particle observed at different azimuth angles by applying the fast projection matching method according to an embodiment of the instance disclosure. FIG. 11B, 11C, 11E, 11F are respectively an explanatory view of a 3D CT reconstructed image of a pyrite particle observed at different azimuth angles by applying a conventional alignment method. FIG. 12A illustrates an explanatory view of a sectional image along a sectional line A-A in FIGS. 11A and 11D, while FIG. 12B, 12C respectively illustrate an explanatory view of a sectional image along a sectional line A-A in FIGS. 11B and 11E, and in FIGS. 11C and 11F.

Figure 13:
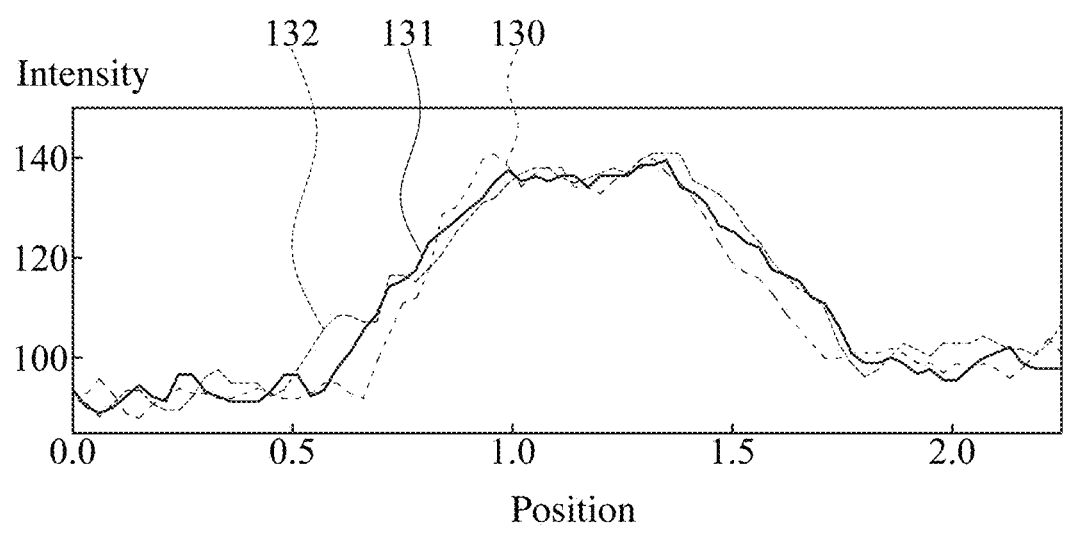
FIG. 13 illustrates an explanatory view of a line section width curve along a sectional line B-B in FIG. 12A-12C.

As shown in FIG. 12A, by applying the fast projection matching method according to the embodiments of the instant disclosure, the reconstructed 3D CT images show the object with much more definite edges than the conventional alignment algorithm. FIG. 13 illustrates an explanatory view of a line section width curve along a sectional line B-B in FIG. 12A-12C. As shown in FIG. 13, the line section width curve 130 of the reconstructed pyrite particle is obviously narrower, the edge responses are much sharper than those line section width curve 131, 132 obtained by the conventional alignment algorithm, which indicates that the fast projection matching method introduced in the embodiments of the instant disclosure has a much higher accuracy to achieve higher spatial resolutions for the reconstructed 3D model.

In an embodiment, when the processing unit 13 calculates the difference value between the intensity distributions, such as Step S08, S14, S16, S18, S20, S22, S198, the processing unit 13 may subtract the intensity distribution by each other, or by comparing the feature points between different intensity distributions to calculate the difference between the intensity distributions. In addition, when the processing unit 13 averages two different intensity distributions, such as Step S15, S17, the processing unit 13 may conduct the cross-correlation algorithm to align the two intensity distributions to each other, and then calculate the average intensity of the two intensity distributions at the same position after both intensity distribution aligned, for producing the average intensity base distribution for the two intensity distributions.

In Step S190, the preset position may be a preset range. The processing unit 13 may calculates the integral of the line section in the preset range. For example, the preset position may be the Y-coordinates between 20 and 40, for producing the intensity distribution within the preset range.

In Steps S192 and S196, the processing unit 13 may conduct the iterative image reconstruction according to any kind of iterative methods, such like Maximum Likelihood Estimation Method (ML-EM) or Simultaneous Iterative Reconstruction Technique (SIRT).

In an embodiment, taking an example that the computed tomography apparatus 10 processes an image of 512-pixels length and 512-pixels width, the total time required for the computed tomography apparatus 10 to produce the computed tomography images is between 250 to 1000 seconds, in which the processing time is only one fortieth of the convention method. The complex conventional alignment processing for the computed tomography images, now becomes much faster.

In brief, according to the embodiments of the instant disclosure, the fast projection matching method for computed tomography images simplifies traditional issues of three-dimensional projection matching into two-dimensional projection matching problem by pre-correcting the Y-axis offsets and $\phi$ shifts of each projection intensity image using common-line method, thereby making the complex CT alignment processing faster and more reliable. This majorly reduces the hardware requirements for CT and data processing, which facilitates the applications in other three dimensional tomographic techniques, such as X-ray micro-CT or electron tomography, and achieves a higher spatial resolution for the reconstructed 3D model.

The two-dimensional projection matching in the second correction procedure may be processed using joint iterative projection matching method that have been demonstrated on traditional three-dimensional projection matching algorithm to dramatically reduce the computational complexity (See Doğa Gürsoy, "Rapid alignment of nanotomography data using joint iterative reconstruction and reprojection", *Scientific Reports* 7, 11818 (2017)). In brief, the iterative projection-matching algorithm processes iterative projection matching and iterative reconstruction, simultaneously. This iterative projection-matching concept can also be utilized in this invention to further speed up the processing time.

While the invention has been described in connection with various aspects, it will be understood that the invention is capable of further modifications. This application is intended to cover any variations, uses or adaptation of the invention following, in general, the principles of the invention, and including such departures from the present disclosure as come within the known and customary practice within the art to which the invention pertains.

What is claimed is:
1. A fast projection matching method for computed tomography images, comprising the steps of:
   (a) capturing a first XY projection intensity image of an object on an XY plane with the object rotating at a first angle corresponding to a rotation axis;

(b) capturing a second XY projection intensity image of the object on the XY plane with the object rotating at a second angle corresponding to the rotation axis;

(c) conducting an integral calculation, along an X-axis direction, on the first XY projection intensity image for calculating a first intensity distribution of the object at the first angle;

(d) conducting the integral calculation, along the X-axis direction, on the second XY projection intensity image for calculating a second intensity distribution of the object at the second angle;

(e) comparing whether the first intensity distribution and the second intensity distribution are identical;

(f) when the first intensity distribution and the second intensity distribution are not identical, rotating the first XY projection intensity image along a Z-axis direction and moving along a Y-axis direction to obtain a first XY projection intensity-modified image, and rotating the second XY projection intensity image along the Z-axis direction and moving along the Y-axis direction to obtain a second XY projection intensity-modified image;

(g) conducting the integral calculation, along the X-axis direction, on the first XY projection intensity-modified image for calculating a first intensity-modified distribution of the object at the first angle, and conducting the integral calculation, along the X-axis direction, on the second XY projection intensity-modified image for calculating a second intensity-modified distribution of the object at the second angle;

(h) balancing a difference value between the first intensity-modified distribution and the second intensity-modified distribution;

(i) when the difference value between the first intensity-modified distribution and the second intensity-modified distribution is greater than a first preset value, repeating the Step (f) to the Step (h) until the difference value between the first intensity-modified distribution and the second intensity-modified distribution is smaller than the first preset value, and when the difference value of the first intensity-modified distribution and the second intensity-modified distribution is smaller than the first preset value, defining the first intensity-modified distribution or the second intensity-modified distribution as an initial intensity base distribution;

(j) capturing a third XY projection intensity image of the object on the XY plane with the object rotating corresponding to the rotation axis at every angle from 0 degree to 180 degree by a preset angle interval;

(k) conducting the integral calculation, along the X-axis direction, on the third XY projection intensity image of the object at each said angle for calculating a third intensity distribution of the object at each said angle;

(l) rotating the third XY projection intensity image of the object along the Z-axis direction at each said angle, for producing a plurality of third XY projection intensity-modified images of the object at each said angle;

(m) conducting the integral calculation, along the X-axis direction, on the third XY projection intensity-modified images of the object at each said angle, for calculating a plurality of third intensity-modified distributions of the object at each said angle;

(n) calculating a first minimum difference intensity distribution with the minimum difference from the third intensity distributions and the third intensity-modified distributions to the initial intensity base distribution;

(o) averaging the first minimum difference intensity distribution of the object at each said angle for producing a first average intensity base distribution;

(p) calculating a second minimum difference intensity distribution of the object at each said angle with the minimum difference from the third intensity distributions and the third intensity-modified distributions to the first average intensity base distribution;

(q) averaging the second minimum difference intensity distribution of the object at each said angle for producing a second average intensity base distribution;

(r) determining whether the difference value between the first average intensity base distribution and the second average intensity base distribution is smaller than a second preset value; and (s) when the difference value between the first average intensity base distribution and the second average intensity base distribution is smaller than the second preset value, rectifying an offset, in the X-axis direction, of the third XY projection intensity image or the third XY projection intensity-modified image in correspondence with the second minimum difference intensity distribution of the object at each said angle, for producing the computed tomography images.

2. The projection matching method of claim 1 further comprising:

(t) when the difference value between the first average intensity base distribution and the second average intensity base distribution is greater than the second preset value, calculating a third minimum difference intensity distribution the object at each said angle with the minimum difference from the third intensity distribution and the third intensity-modified distribution to the second average intensity base distribution;

(u) averaging the third minimum difference intensity distribution of the object at each said angle for producing a third average intensity base distribution;

(v) determining whether the difference value between the second average intensity base distribution and the third average intensity base distribution is smaller than the second preset value; and (w) when the difference value between the second average intensity base distribution and the third average intensity base distribution is smaller than the second preset value, rectifying an offset in the X-axis direction of the third XY projection intensity image or the third XY projection intensity-modified image in correspondence with the third minimum difference intensity distribution of the object at each said angle for producing the computed tomography images.

3. The projection matching method of claim 1, wherein the Step (s) comprising:

calculating a line section intensity distribution, of the third XY projection intensity image or the third XY projection intensity-modified image in correspondence with the second minimum difference intensity distribution with the object rotated corresponding to the rotation axis at each said angle from 0 degree to 180 degree, at a preset position in the Y-axis direction;

aligning, along the X-axis direction with a cross-correlation algorithm, the line section intensity distribution of the object at each said angle;

image-reconstructing, with an iterative reconstruction algorithm, according to the aligned line section intensity distribution of the object at each said angle, for producing a first reconstructed image; and producing the computed tomography images according to the first reconstructed image.

4. The projection matching method of claim 3, wherein the Step (s) further comprising:

conducting the integral calculation on the first reconstructed image by the preset angle interval in the Z-axis direction, for calculating a fourth intensity distribution of the first reconstructed image rotated corresponding to the rotation axis at each said angle from 0 degree to 180 degree;

one-by-one aligning the line section intensity distribution of the object at each said angle respectively along the X-axis direction, to the fourth intensity distribution at each said same angle;

image-reconstructing, by the iterative reconstruction algorithm and according to the line section intensity distribution respectively aligned to the fourth intensity distribution of the object at each said angle, for producing a second reconstructed image;

respectively conducting the integral calculation on the second reconstructed image by the preset angle interval along the Z-axis direction, for calculating a fifth intensity distribution of the second reconstructed image rotated corresponding to the rotation axis at each said angle from 0 degree to 180 degree;

determining whether the difference value between the fifth intensity distribution and the fourth intensity distribution is smaller than a third preset value; and when the difference value between the fifth intensity distribution and the fourth intensity distribution is smaller than the third preset value, producing the computed tomography images according to the second reconstructed image.

5. The projection matching method of claim 4, wherein the Step (s) further comprising:

when the difference value between the fifth intensity distribution and the fourth intensity distribution is greater than the third preset value, one-by-one aligning the line section intensity distribution of the object at each said angle respectively along the X-axis direction, to the fifth intensity distribution at each said same angle;

image-reconstructing, by the iterative reconstruction algorithm and according to the line section intensity distribution aligned to the fifth intensity distribution of the object at each said angle, for producing a third reconstructed image;

conducting the integral calculation on the third reconstructed image by the preset angle interval along the Z-axis direction, for calculating a sixth intensity distribution of the third reconstructed image rotated corresponding to the rotation axis at each said angle from 0 degree to 180 degree;

determining whether the difference value between the sixth intensity distribution and the fifth intensity distribution is smaller than the third preset value; and when the difference value between the sixth intensity distribution and the fifth intensity distribution is smaller than the third preset value, producing the computed tomography images according to the third reconstructed image.

6. The projection matching method of claim 1, wherein the Step (o) comprising:

aligning, with the cross-correlation algorithm, the first minimum difference intensity distribution of the object at each said angle; and averaging an intensity value at the same position as the aligned first minimum difference intensity distribution of the object at each said angle, for producing the first average intensity base distribution.

7. The projection matching method of claim 1, wherein in the Step (h):

directly subtracting the first intensity-modified distribution and the second intensity-modified distribution from each other, or comparing feature points between the first intensity-modified distribution and the second intensity-modified distribution, for balancing the difference value between the first intensity-modified distribution and the second intensity-modified distribution.

* * * * *